United States Patent [19]
Gaviraghi et al.

[11] Patent Number: 6,071,939
[45] Date of Patent: Jun. 6, 2000

[54] MEDICAMENTS FOR THE TREATMENT OF HYPERTENSION

[75] Inventors: Giovanni Gaviraghi; Mauro Quartaroli, both of Verona, Italy

[73] Assignees: Glaxo Group Limited, Greenford, United Kingdom; Boehringer Ingelheim GmbH, Ingelheim am Rhein, Germany

[21] Appl. No.: 09/304,884

[22] Filed: May 4, 1999

[30] Foreign Application Priority Data

Nov. 6, 1998 [WO] WIPO ................. PCT/GB98/03336

[51] Int. Cl.⁷ .................... A61K 31/44; A61K 31/415
[52] U.S. Cl. ........................... 514/356; 514/397
[58] Field of Search ................... 514/356, 397

[56] References Cited

U.S. PATENT DOCUMENTS

| | | |
|---|---|---|
| 4,801,599 | 1/1989 | Semeraro et al. . |
| 5,591,762 | 1/1997 | Hauel et al. . |
| 5,594,003 | 1/1997 | Hauel et al. . |
| 5,602,127 | 2/1997 | Hauel et al. . |
| 5,614,519 | 3/1997 | Hauel et al. . |

FOREIGN PATENT DOCUMENTS

| | | |
|---|---|---|
| 0 502 314 | 9/1992 | European Pat. Off. . |
| WO 96/07400 | 3/1996 | WIPO . |
| WO 96/19233 | 6/1996 | WIPO . |
| WO 97/36874 | 10/1997 | WIPO . |
| WO 98/30216 | 7/1998 | WIPO . |
| WO 98/40067 | 9/1998 | WIPO . |

OTHER PUBLICATIONS

Scrip No. 2336, May 20, 1998, p. 9.
Y. Fijimura et al., *Japanese Pharmacology and Therapeutics* 23(12): 887–93 (1995) (abstract).
P. Prasad et al., *American Journal of Hypertension* 10(4): 2 (Apr. 1997).
D. Neefe et al., *American Journal of Hypertension* 10(4): 2 (Apr. 1997).
G. MacGreggor et al., *American Journal of Hypertension* 10(4): 2 (Apr. 1997).
Dd. Wirth, *Journal of Pharmaceutical Sciences* 87(1):31 (Jan. 1998).
International Search Report for PCT/GB98/03336, dated Jul. 12, 1998.

*Primary Examiner*—Raymond Henley, III
*Attorney, Agent, or Firm*—Lorie Ann Morgan

[57] ABSTRACT

A composition comprising diethyl (E)-4-[2-[(tert-butyloxycarbonyl)vinyl]phenyl-1,4-dihydro-2,6-dimethylpyridine-3,5-dicarboxylate (lacidipine) and 4'-[[2-n-propyl-4-methyl-6 -(1-methylbenziimidazol-2-yl)-benzimidazol-1-yl]-methyl]-biphenyl-2 -carboxylic acid (telmisartan) or a physiologically functional derivative thereof.

8 Claims, No Drawings

MEDICAMENTS FOR THE TREATMENT OF HYPERTENSION

The present invention relates to therapeutic combinations comprising diethyl (E)-4-[2-[(tert-butyloxycarbonyl)vinyl] phenyl-1,4-dihydro-2,6-dimethylpyridine-3,5-dicarboxylate (lacidipine) and 4'-[[2-n-propyl-4-methyl-6-(1-methylbenziimidazol -2-yl)-benzimidazol-1-yl]-methyl]-biphenyl-2-carboxylic acid (telmisartan), to pharmaceutical compositions containing said combinations and their use in the treatment of cardiovascular disorders including hypertension.

Lacidipine, which is described in British patent no. 2164336, is a potent long acting calcium antagonist which is particularly useful for treating hypertension. The compound may be also useful for the treatment of other cardiovascular disorders including atherosclerosis, peripheral vascular disease, ischaemic heart disease and congestive heart failure.

Telmisartan, which is described in European patent no. 0502314, is an angiotensin-ll-antagonist which is useful for treating hypertension and cardiac insufficiency and for treating other cardiovascular disorders including ischaemic peripheral circulation disorders, myocardial ischaemia (angina).

European patent no. 0502314 teaches that the angiotensin-ll-antagonists described therein may be administered in combination with other active substances including calcium antagonists. There is however no specific disclosure of such combinations with lacidipine.

We have found that the combination of lacidipine and telmisartan provides a useful and unexpectedly advantageous combination for the treatment of cardiovascular disorders, such as hypertension, atherosclerosis and ischaemic heart disease.

In particular it has now been found that by combining lacidipine and telmisartan, synergistic antihypertensive effect is achieved. It is a feature of this invention that the use of such a drug combination will provide one or more of the following effects: synergistic antihypertensive effects, antihypertensive effect over a longer period and/or allow a better management of any potential drug-related side effects. Furthermore, the improvement of blood pressure control achieved by using such a drug combination may afford a better protection from the associated diseases which are induced by hypertension.

According to one aspect of the invention there is provided a combination comprising lacidipine and telmisartan or a physiologically functional derivative thereof and more particularly a combination comprising lacidipine and telmisartan.

As used herein, the term "*physiologically functional derivative*" includes any physiologically acceptable solvate, salt, ester, salt of such ester, or solvates of any such salt or ester, of telmisartan.

Preferred esters in accordance with the invention are independently selected from the following group: (1) carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy), or amino; (2) sulphonate esters, such as alkyl- or aralkylsulphonyl (for example, methanesulphonyl); (3) amino acid esters (for example, L-valyl or L-isoleucyl); and (4) phosphonate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Examples of physiologically acceptable salts include salts derived from an appropriate base, such as an alkali metal (for example, sodium), an alkaline earth (for example, magnesium), ammonium and $NX_4^+$ (wherein X is $C_{1-4}$ alkyl) or ammonium salts, formed with amino acids (e.g lysine and arginine) and organic bases (e.g procaine, phenylbenzylamine, ethanolamine and N-methyl glucosamine). Salts of acids or bases which are not physiologically acceptable may also find use, for example, in the preparation or purification of a physiologically acceptable compound. All salts, whether or not derived from a physiologically acceptable acid or base, are within the scope of the present invention.

The present invention thus provides a method for the treatment of hypertension in a mammal including a human, which comprises treating said animal with a therapeutically effective amount of a combination of lacidipine and telmisartan or a physiologically functional derivative thereof.

Reference herein to treatment extends to prophylaxis as well as the treatment of established hypertension or symptoms.

It will be appreciated that the compounds of the combination or composition may be administered simultaneously, either in the same or different pharmaceutical formulations or sequentially. If there is sequential administration, the delay in administering the second and any subsequent active ingredient should not be such as to lose the benefit of a synergistic therapeutic effect of the combination of the active ingredients. It will also be understood that the compounds of the combination or the physiologically functional derivatives of any thereof, whether presented simultaneously or sequentially, may be administered individually or in multiples or in any combination thereof.

According to another aspect, the present invention provides the use of lacidipine in the manufacture of a medicament for administration simultaneously or sequentially with telmisartan or a physiologically functional derivative thereof for the treatment and/or prophylaxis of hypertension.

The synergistic effects of the combination of lacidipine and telmisartan may be seen over a wide ratio of combinations, for example, of 1:100 to 1:1, such as 1:50 to 1:2 (lacidipine:telmisartan by weight), preferably of 1:40 to 1:3.33 (lacidipine:telmisartan by weight). Examples of such combinations include those wherein the ratio (lacidipine:telmisartan by weight) of lacidipine to telmisartan is 1.1.5; 1:5; 1:10, 1:20; 1:40; 1:6.67 or 1:13.33. Conveniently each compound will be employed in the combination in an amount at which it exhibits an antihypertensive effect when used alone.

The amount of a combination of lacidipine and telmisartan required to be effective as antihypertensive may, of course, vary and is ultimately at the discretion of the medical practitioner. The factors to be considered include the route of administration and nature of the formulation, the animal's body weight, age and general condition and the nature and severity of the disease to be treated.

In general a suitable dose of lacidipine for administration to a human for the treatment of hypertension may be in the range of 0.1 to 10 mg per day, preferably in the range of 1 to 6 mg per day and most preferably in the range 2–6 mg per day. Lacidipine is advantageously administered by oral route once a day.

In general, a suitable dose of telmisartan for administration to a human may be in the range of 5 to 120 mg per day, advantageously in the range of 20 to 80 mg per day. Telmisartan is advantageously administered by oral route once a day.

Unless otherwise indicated all weights of active ingredients are calculated in terms of the drug per se. The desired dose may preferably be presented as one, two, three, four, five, six or more sub-doses administered at appropriate intervals throughout the day. Conveniently lacidipine and telmisartan are administered as a single daily dose.

The components of the combination which may be referred to as active ingredients may be administered for therapy to an animal e.g. a mammal including a human in a conventional manner.

While it is possible for the active ingredients of the combination to be administered as the raw chemical it is preferable to present them as a pharmaceutical formulation. Pharmaceutical formulations according to the present invention comprise a combination according to the invention together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately they are generally each presented as a pharmaceutical formulation. The references hereinafter to formulations refer, unless otherwise stated, to formulations containing either the combination or a component thereof.

A combination of lacidipine and telmisartan or a physiologically functional derivative thereof may conveniently be presented as a pharmaceutical formulation in a unitary dosage form. A convenient unitary dosage formulation contains lacidipine in an amount from 1 mg to 6 mg and telmisartan in an amount from 10 mg to 100 mg. A particularly convenient unitary dosage formulation contains lacidipine in an amount from 2 mg to 6 mg, more particularly in an amount from 2 mg to 4 mg, and telmisartan in amount from 20 mg to 80 mg.

Pharmaceutical formulations are often prescribed to the patient in "patient kit-packs" containing the whole course of treatment in a single package, usually a blister pack. Patient kit-packs have an advantage over traditional prescriptions, where a pharmacist divides a patient's supply of a pharmaceutical from a bulk supply, in that the patient always has access to the package insert contained in the patient kit-pack, normally missing in traditional prescriptions. The inclusion of a package insert has been shown to improve patient compliance with the physician's instructions and, therefore, lead generally to more successful treatment.

It will be understood that the administration of the combination of the invention by means of a single patient kit-pack, or patient kit-packs of each formulation, containing within a package insert instructing the patient to the correct use of the invention is a desirable additional feature of this invention.

According to a further aspect of the invention provided is a multiple, for example, double or triple, kit-pack comprising at least lacidipine and telmisartan or a physiologically functional derivative thereof and an information insert containing directions on the use of the combination of the invention.

Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, sodium croscarmellose cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored any may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising, for example, cocoa butter or polyethylene glycols.

Topical administration may also be by means of a transdermal iontophoretic device.

Formulations suitable for vaginal administration may be presented as tablets, pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Formulations suitable for parenteral administration include aqueous and nonaqueous isotonic sterile injection solutions which may contain anti-oxidants, buffers, preservatives and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The pharmaceutical composition of the invention containing the two active ingredients may be prepared according to conventional techniques well known in the pharmaceutical industry. Thus, for example the lacidipine and telmisartan may be admixed together with suitable excipients such as those described above for the formulation of each of the active ingredients separately. Tablets may be prepared, for example by direct compression of such a mixture or using other conventional methods. Bilayer tablets may be prepared according to conventional procedure. Thus, for example, by separately compressing the two blends in a suitable tabletting machine with two filling stations. Capsules may be prepared by filling the blend along with suitable excipients into gelatin capsules, using a suitable filling machine. Controlled release forms for oral or rectal administration may be formulated in a conventional manner associated with controlled release forms.

Biological Data

The advantageous profile of the antihypertensive activity obtained with the administration of lacidipine with telmisartan may be demonstrated in male spontaneously hypertensive rats. In the following experiments lacidipine and telmisartan were administered as a suspension in 0.5% Methocel™ (Hydroxypropyl methyl cellulose) by oral gavage.

Experiment 1

Lacidipine (0.2 mg/kg), telmisartan (1 mg/kg) and a combination of lacidipine (0.2 mg/kg ) and telmisartan (1 mg/kg) were administered. After dosing, mean blood pressure (MBP) and heart rate (HR) variations were calculated at fixed intervals and expressed as a percentage of pre-drug values. The results obtained three hours after administration of lacidipine and telmisartan, alone or in combination, are summarised in table 1.

TABLE 1

| | Compound | | |
|---|---|---|---|
| | lacidipine 0.2 mg/kg | telmisartan 1 mg/kg | lacidipine 0.2 mg/kg telmisartan 1 mg/kg |
| MBP | −13.8 ± 5.4 | −4.5 ± 8.2 | −30.5 ± 5.0 |
| HR | 1.9 ± 6.4 | 2.7 ± 17.0 | 12.6 ± 23.1 |

The reduction in mean blood pressure with the combination of lacidipine and telmisartan was significantly greater than was to be expected and this was also achieved without a significant effect on the heart rate.

Experiment 2

Vehicle (Methocel™ 0.5% (10 ml/kg), lacidipine (0.2 mg/kg) and telmisartan (0.3 mg/kg) and a combination of lacidipine(0.2 mg/kg) and telmisartan(0.3 mg/kg) were administered to male spontaneously hypertensive rats.

The effects on the blood pressure and heart rate (HR) were monitored for 24 hours. The results obtained in terms of area under the curve for lowering diastolic blood pressure (DBP) and changes in HR within 24 hours of treatment (AUC 0-24), calculated using the mean percentage of variation from baseline data taken at various time interval, are summarised in Table 2.

TABLE 2

| | Compound | | | |
|---|---|---|---|---|
| | vehicle | lacidipine 0.2 mg/kg | telmisartan 0.3 mg/kg | lacidipine 0.2 mg/kg telmisartan 0.3 mg/kg |
| DBP ($ACU_{0-24}$) | 1.17 ± 10.39 | 0.89 ± 4.58 | 0.05 ± 4.81 | −15.5 ± 5.52 |
| HR ($AUC_{0-24}$) | 4.22 ± 3.50 | 3.76 ± 8.24 | 6.25 ± 8.51 | 6.50 ± 8.57 |

The above data show that lacidipine and telmisartan when administered alone did not induce statistically significant variations in DBP AUC (0-24) and in HR AUC (0-24) compared to vehicle-treated rats. On the contrary, when the combination of lacidipine and telmisartan was administered, a statistically significant reduction in DBP AUC (0-24) was achieved. In particular, DBP AUC (0-24) reduction was significantly greater than that predicted from the sum of the monotherapy response. Furthermore, the combination does not significantly increase HR. Consequently, tachycardia was not observed. The combination of lacidipine and telmisartan also improves the duration of action up to 24 hours after treatment.

Experiment 3

Lacidipine (0.2 mg/kg) and telmisartan (0.3 mg/kg) alone or in combination were administered once daily for 5 days and the effects on blood pressure and heart rate were detected. The results obtained in terms of area under the curve for lowering diastolic blood pressure DBP AUC and changes in HR (HR AUC) calculated every day for the whole duration of the experiments are summarised in table 3.

TABLE 3

| | Compound | | | |
|---|---|---|---|---|
| | vehicle | lacidipine 0.2 mg/kg | telmisartan 0.3 mg/kg | lacidipine 0.2 mg/kg telmisartan 0.3 mg/kg |
| DBP (AUC) | −5.07 ± 8.43 | −9.15 ± 9.79 | −15.72 ± 12.04 | −25.48 ± 8.26 |
| HR (AUC) | 5.57 ± 11.09 | 13.84 ± 23.92 | 4.74 ± 11.27 | 3.49 ± 14.85 |

According to table 3, data show that lacidipine and telmisartan administered alone induce a statistically significant decrease in DBP AUC compared with vehicle -treated rats. When lacidipine and telmisartan were administered in combination a statistically significant effect was achieved in DBP AUC compared to vehicle treated rats. Furthermore, DBP AUC was significantly greater than that predicted from the sum of the monotherapy response. The combination also does not significantly increase HR.

The compounds of the combination of the present invention may be obtained in a conventional manner.

Lacidipine may be prepared by the method described in British Patent N°. 2164336 which is incorporated herein by reference hereto.

Telmisartan or a physiologically functional derivative thereof may be prepared by the method described in European Patent N°. 502314 which is incorporated herein by reference or by known methods described for analogous compounds.

For co-administration the lacidipine and telmisartan may be formulated in a conventional manner. Thus for example lacidipine may be formulated as described in British Patent N°. 2164336 and telmisartan may be formulated as described in European Patent N°. 0502314.

In a preferred aspect of the invention lacidipine and telmisartan are formulated in a single pharmaceutical composition.

In order that this aspect of the invention may be more fully understood the following examples are given by way of illustration only.

TABLET FORMULATIONS

EXAMPLE 1

The following formulation was prepared by mixing lacidipine granulated containing monohydrate lactose and telmisartan spray dried granulate with sorbitol, followed by addition of magnesium stearate and compression.

|  | mg/tablet |
| --- | --- |
| Lacidipine | 4 |
| Telmisartan | 40 |
| Monohydrate Lactose | 197 |
| Sodium Hydroxide | 3.36 |
| Meglumine | 12 |
| Povidone | 52 |
| Sorbitol | 184 |
| Magnesium Stearate | 7.5 |

EXAMPLE 2

The following formulation was prepared by mixing telmisartan spray dried granule with sorbitol and magnesium stearate. Then lacidipine granule was mixed with the remaining magnesium stearate and eventually with sorbitol. The two blends were seperately compressed in a suitable tabletting machine with two filling stations to produce bilayer tablets.

|  | mg/tablet |
| --- | --- |
| Telmisartan | 40 |
| Lacidipine | 4 |
| Povidone | 40 |
| Monohydrate Lactose | 197 |
| Sodium Hydroxide | 3.36 |
| Meglumine | 12 |
| Povidone | 12 |
| Sorbitol | 184.1 |

The following formulations (Examples 3a–3d) may be prepared by mixing a granulate containing lacidipine, sorbitol and povidone with telmisartan spray dried granulate, sorbitol, followed by addition of magnesium stearate and compression.

EXAMPLE 3a

|  | mg/tablet |
| --- | --- |
| Telmisartan | 40 |
| Lacidipine | 4 |
| Povidone | 52 |
| Sorbitol | 116 |
| Sodium Hydroxide | 3.36 |
| Meglumine | 12 |
| Sorbitol | 117.64 |
| Magnesium Stearate | 5 |

EXAMPLE 3b

|  | mg/tablet |
| --- | --- |
| Telmisartan | 20 |
| Lacidipine | 2 |
| Povidone | 26 |
| Sorbitol | 138 |
| Sodium Hydroxide | 1.68 |
| Meglumine | 6 |
| Sorbitol | 151.32 |
| Magnesium Stearate | 5 |

EXAMPLE 3c

|  | mg/tablet |
| --- | --- |
| Telmisartan | 80 |
| Lacidipine | 2 |
| Povidone | 44 |
| Sorbitol | 138 |
| Sodium Hydroxide | 6.72 |
| Meglumine | 24 |
| Sorbitol | 50.28 |
| Magnesium Stearate | 5 |

EXAMPLE 3d

|  | mg/tablet |
| --- | --- |
| Telmisartan | 80 |
| Lacidipine | 6 |
| Povidone | 84 |
| Sorbitol | 94 |
| Sodium Hydroxide | 6.72 |
| Meglumine | 24 |
| Sorbitol | 50.28 |
| Magnesium Stearate | 5 |

EXAMPLE 4

The following formulation was prepared by granulating telmisartan spray dried granule and sorbitol with lacidipine and povidone followed by addition of sorbitol and magnesium stearate and compression.

|  | mg/tablet |
| --- | --- |
| Lacidipine | 4 |
| Povidone | 40 |
| Sorbitol | 88.64 |
| Telmisartan | 40 |
| Sodium Hydroxide | 3.36 |
| Meglumine | 12 |
| Povidone | 12 |
| Sorbitol | 295 |
| Magnesium Stearate | 5 |

EXAMPLE 5

The following formulation was prepared by mixing lacidipine granulated containing sorbitol and colloidal silica and telmisartan spray dried granulate with sorbitol, followed by addition of magnesium stearate and compression

|  | mg/tablet |
| --- | --- |
| Telmisartan | 40 |
| Lacidipine | 4 |
| Povidone | 52 |
| Sorbitol | 112.5 |
| Amorphous Silica | 3.50 |
| Sodium Hydroxide | 3.36 |
| Meglumine | 12 |
| Sorbitol | 117.4 |
| Magnesium Stearate | 5 |

What is claimed is:

1. A composition comprising diethyl (E)-4-[2-[(tert-butyloxycarbonyl)vinyl]phenyl-1,4-dihydro-2,6-dimethylpyridine-3,5-dicarboxylate (lacidipine) and 4'-[[2-n-propyl-4-methyl-6-(1-methylbenziimidazol-2-yl)-benzimidazol-1-yl]-methyl]-biphenyl-2-carboxylic acid (telmisartan) or a physiologically functional derivative thereof.

2. A composition according to claim 1 wherein the ratio of lacidipine to telmisartin is from 1:100 to 1:1 by weight.

3. A pharmaceutical formulation comprising a composition according to claim 1 together with one or more pharmaceutically acceptable carriers or excipients.

4. A pharmaceutical formulation according to claim 3 in a unitary dosage form.

5. A patient kit-pack comprising lacidipine and telmisartan or a physiologically functional derivative thereof.

6. A method for the treatment or prophylaxis of hypertension in a mammal which comprises treating said animal with a therapeutically effective amount of a composition as claimed in claim 1.

7. A method according to claim 6 wherein the composition is administered as a single combined formulation.

8. A method for the treatment of cardiovascular disorders in a mammal which comprises treating said animal with a therapeutically effective amount of a composition as claimed in claim 1.

* * * * *